United States Patent
Tamura et al.

(10) Patent No.: US 9,943,284 B2
(45) Date of Patent: Apr. 17, 2018

(54) INFORMATION PROCESSING SYSTEM, INFORMATION PROCESSING METHOD, AND PROGRAM

(71) Applicant: CANON KABUSHIKI KAISHA, Tokyo (JP)

(72) Inventors: Toshikazu Tamura, Utsunomiya (JP); Akiya Nakayama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/186,055

(22) Filed: Jun. 17, 2016

(65) Prior Publication Data

US 2016/0374640 A1    Dec. 29, 2016

(30) Foreign Application Priority Data

Jun. 23, 2015 (JP) ................ 2015-125895

(51) Int. Cl.
  *G06F 9/32* (2006.01)
  *A61B 6/00* (2006.01)

(52) U.S. Cl.
  CPC .............. *A61B 6/566* (2013.01); *A61B 6/547* (2013.01); *A61B 6/563* (2013.01); *A61B 6/4494* (2013.01)

(58) Field of Classification Search
  CPC ........ A61B 6/566; A61B 6/563; A61B 6/4494
  See application file for complete search history.

(56) References Cited

U.S. PATENT DOCUMENTS

| | | | |
|---|---|---|---|
| 9,412,257 B2 * | 8/2016 | Tajima | G08B 13/22 |
| 9,501,430 B2 * | 11/2016 | Guillemin | A61B 6/4494 |
| 9,725,930 B2 * | 8/2017 | Vroom | E05B 73/0082 |
| 2004/0088193 A1 * | 5/2004 | Moriyama | G06F 19/321 |
| | | | 705/3 |
| 2004/0103344 A1 * | 5/2004 | Stephens | G06F 11/2635 |
| | | | 714/18 |
| 2010/0054406 A1 * | 3/2010 | Kitano | G01N 23/04 |
| | | | 378/62 |
| 2010/0054417 A1 * | 3/2010 | Nishino | A61B 6/00 |
| | | | 378/98.8 |

(Continued)

FOREIGN PATENT DOCUMENTS

JP     2012-165919 A    9/2012

*Primary Examiner* — Joseph Feild
*Assistant Examiner* — Rufus Point
(74) *Attorney, Agent, or Firm* — Canon U.S.A., Inc. IP Division

(57) ABSTRACT

An information processing system including an information processing apparatus that receives captured radiographic images captured by a plurality of image capturing apparatuses each having a wireless communication function and a wired apparatus that connects to the information processing apparatus in a wired manner, the information processing system includes a setting unit that sets, in a case where one of the plurality of image capturing apparatuses is connected to the wired apparatus, the connected image capturing apparatus as a master unit of wireless communication, and a communication unit that receives, via the image capturing apparatus set as the master unit, a captured image of a different image capturing apparatus that is received through wireless communication by the image capturing apparatus set as the master unit from the different image capturing apparatus set as a slave unit of wireless communication.

14 Claims, 8 Drawing Sheets

(56) References Cited

U.S. PATENT DOCUMENTS

| | | | | |
|---|---|---|---|---|
| 2011/0057111 A1* | 3/2011 | Nishino | ............... | G01T 7/00 |
| | | | | 250/370.08 |
| 2012/0206233 A1 | 8/2012 | Kamiya | ............ | A61B 6/4283 |
| | | | | 340/2.1 |
| 2012/0207278 A1* | 8/2012 | Yonekawa | ......... | A61B 6/4233 |
| | | | | 378/98.5 |
| 2012/0208576 A1* | 8/2012 | Kamiya | ............ | A61B 6/4283 |
| | | | | 455/500 |
| 2013/0266152 A1* | 10/2013 | Haynie | ............. | H04R 5/033 |
| | | | | 381/80 |
| 2013/0329860 A1* | 12/2013 | Nonaka | ........... | G06F 19/3418 |
| | | | | 378/91 |
| 2014/0257330 A1* | 9/2014 | Choi | ............. | A61B 19/2203 |
| | | | | 606/130 |
| 2014/0275954 A1* | 9/2014 | Ohta | ............. | A61B 6/465 |
| | | | | 600/407 |
| 2014/0276056 A1* | 9/2014 | Ohta | ............. | A61B 90/00 |
| | | | | 600/440 |
| 2015/0223767 A1* | 8/2015 | Sehnert | ............. | A61B 6/06 |
| | | | | 378/42 |
| 2015/0279196 A1* | 10/2015 | Tajima | ............. | G08B 13/22 |
| | | | | 340/539.32 |
| 2016/0022231 A1* | 1/2016 | Nonaka | ............. | A61B 6/4405 |
| | | | | 250/393 |
| 2016/0345920 A1* | 12/2016 | Tajima | ............. | H04N 5/32 |
| 2016/0374640 A1* | 12/2016 | Tamura | ............. | A61B 6/566 |
| | | | | 340/2.1 |

* cited by examiner

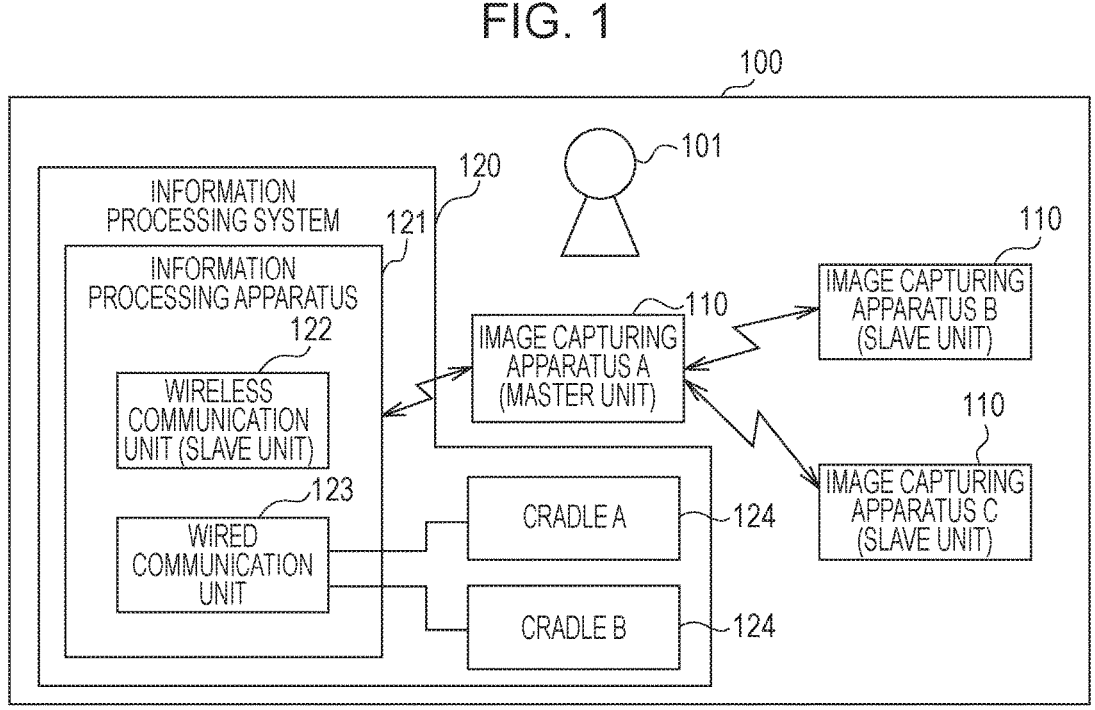
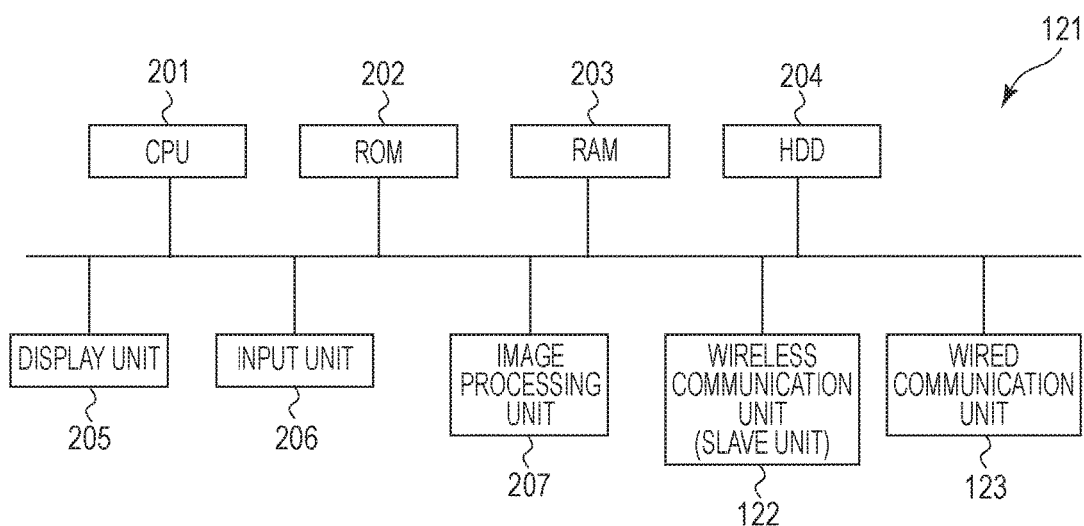

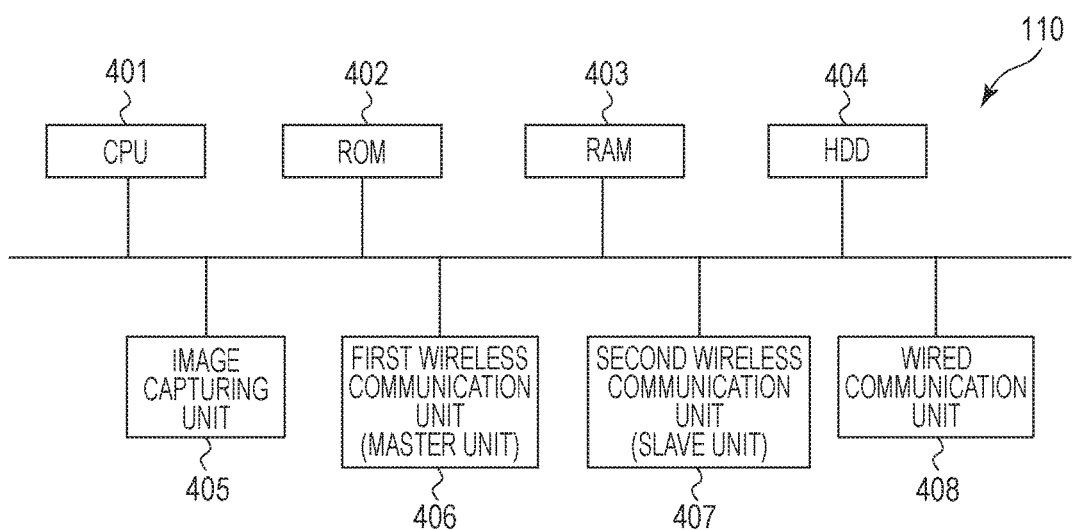

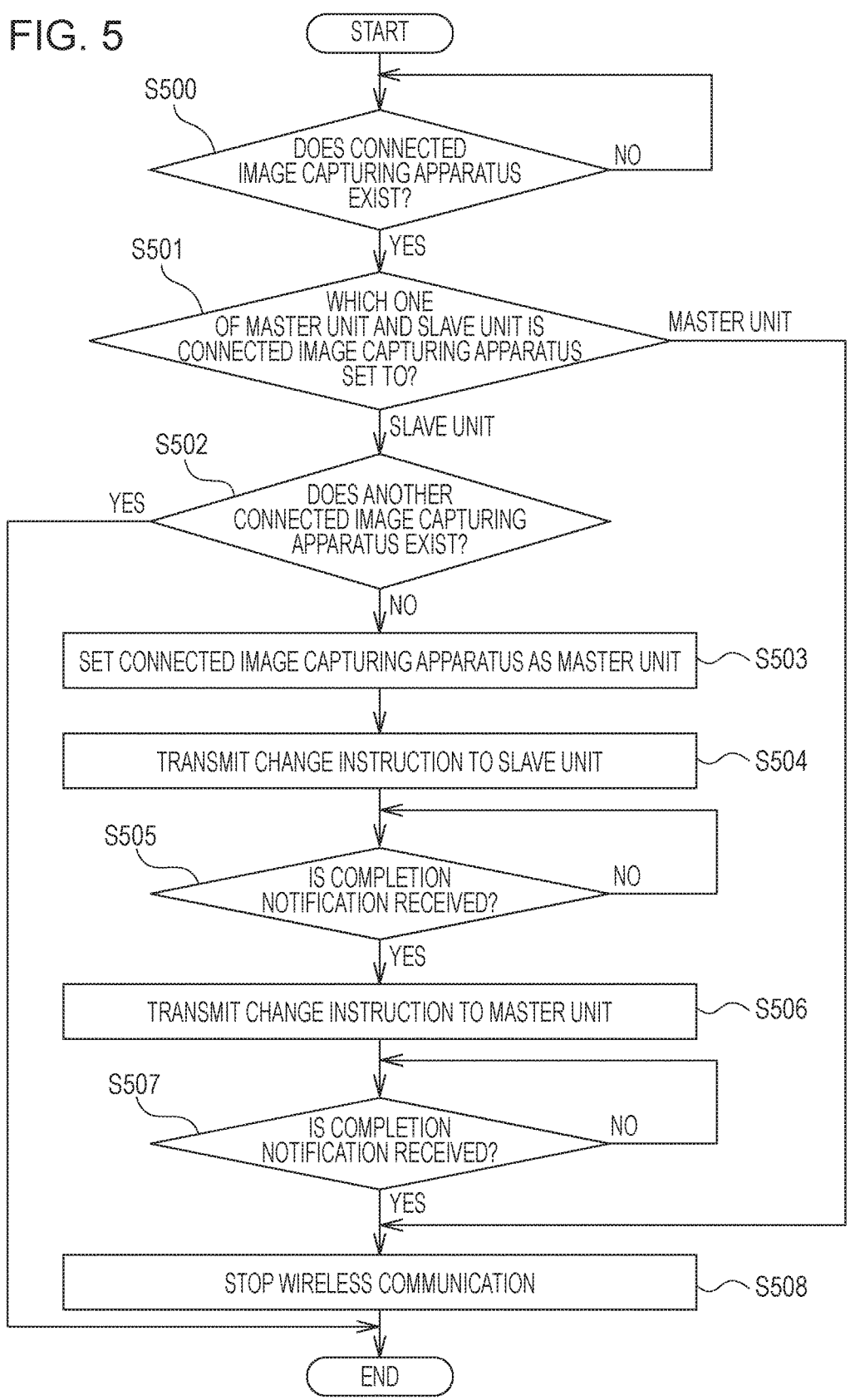

FIG. 6A
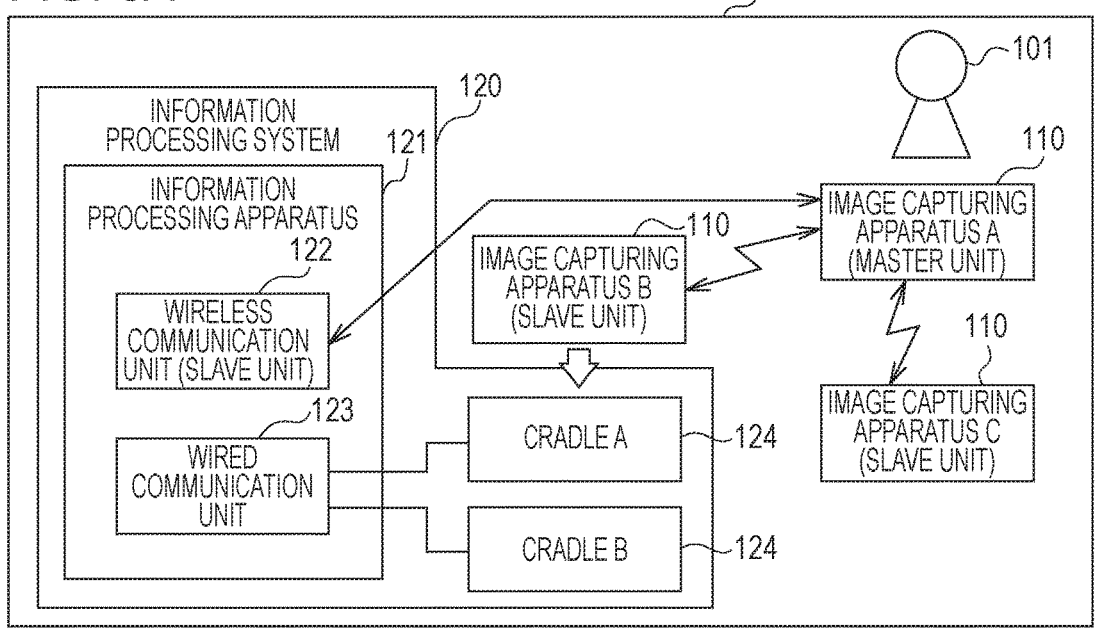
FIG. 6B
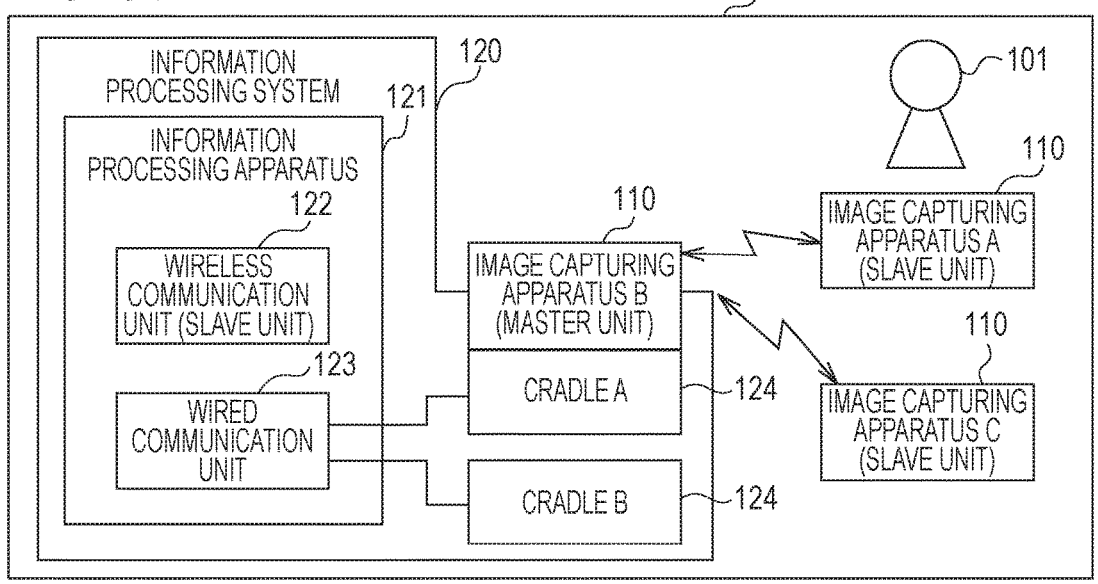
FIG. 6C
| APPARATUS ID | SETTING INFORMATION |
|---|---|
| a | SLAVE UNIT |
| b | MASTER UNIT |
| c | SLAVE UNIT |
300

INFORMATION PROCESSING SYSTEM, INFORMATION PROCESSING METHOD, AND PROGRAM

BACKGROUND

Field

Aspects of the present invention generally relate to an information processing system, an information processing method, and a program.

Description of the Related Art

Hitherto, radiographic image capturing systems have been commercialized in which a radiographic image is generated by performing image processing on a digital radiographic image obtained by digitalizing a radiographic image, which is an intensity distribution of radiation obtained by being irradiated with radiation such as X-rays from a radiation generator and transmitting the radiation through an object. For example, in X-ray imaging systems, an X-ray generator performs application of X-rays, and an X-ray image capturing apparatus acquires image data and transfers the image data to an image acquisition computer for image processing and storing. The image acquisition computer displays an image that has been subjected to image processing on a display device.

In recent years, a technique has been regarded as mainstream in which an X-ray image capturing apparatus transfers an acquired image to a computer using radio based on IEEE 802.11 standards or the like so that the image may be processed and stored. The X-ray image capturing apparatus that performs wireless communication is connected to a dedicated access point (hereinafter, referred to as an AP), and transmits data via the AP. Furthermore, the X-ray image capturing apparatus may include an AP function instead of using a dedicated AP.

Japanese Patent Laid-Open No. 2012-165919 discloses a technique in which wireless communication is tried with a console as a communication target in an infrastructure mode in the case where a designation for performing communication in the infrastructure mode is provided and wireless communication is performed in an ad-hoc mode in the case where communication is impossible.

However, the X-ray image capturing apparatus provided with the AP function is movable and the location where the X-ray image capturing apparatus is installed may not be fixed. In this case, wireless communication becomes unstable depending on the location of the X-ray image capturing apparatus. Furthermore, in the case where radiographing is performed using an X-ray image capturing apparatus that is not provided with the AP function, an obtained captured image may be transmitted to an image acquisition computer via an X-ray image capturing apparatus that is provided with the AP function. In this case, two wireless communication paths, that is, a path between the apparatus not provided with the AP function and the apparatus provided with the AP function and a path between the apparatus provided with the AP function and the computer, are present. Therefore, the communication speed decreases depending on the location of the apparatuses and the computer.

SUMMARY OF THE INVENTION

An aspect of the present invention is to achieve transmission of a captured image via a stable path while preventing the communication speed from decreasing.

An information processing system including an information processing apparatus configured to receive captured radiographic images captured by a plurality of image capturing apparatuses each having a wireless communication function and a wired apparatus configured to be connected to the information processing apparatus in a wired manner, the information processing system includes a setting unit configured to set, in a case where one of the plurality of image capturing apparatuses is connected to the wired apparatus, the connected image capturing apparatus as a master unit of wireless communication, and a communication unit configured to receive, via the image capturing apparatus set as the master unit by the setting unit, a captured image of a different image capturing apparatus that is received through wireless communication by the image capturing apparatus set as the master unit from the different image capturing apparatus set as a slave unit of wireless communication.

Further features of aspects of the present invention will become apparent from the following description of exemplary embodiments with reference to the attached drawings.

BRIEF DESCRIPTION OF THE DRAWINGS

FIG. 1 is an overall configuration diagram of a radiographing system.

FIG. 2 is a diagram illustrating a hardware configuration of an information processing apparatus.

FIG. 3 is a diagram illustrating an example of an AP table.

FIG. 4 is a diagram illustrating a hardware configuration of an image capturing apparatus.

FIG. 5 is a flowchart illustrating a communication management process.

FIGS. 6A, 6B, and 6C are explanatory diagrams of a communication management process.

DESCRIPTION OF THE EMBODIMENTS

Figure 7A:
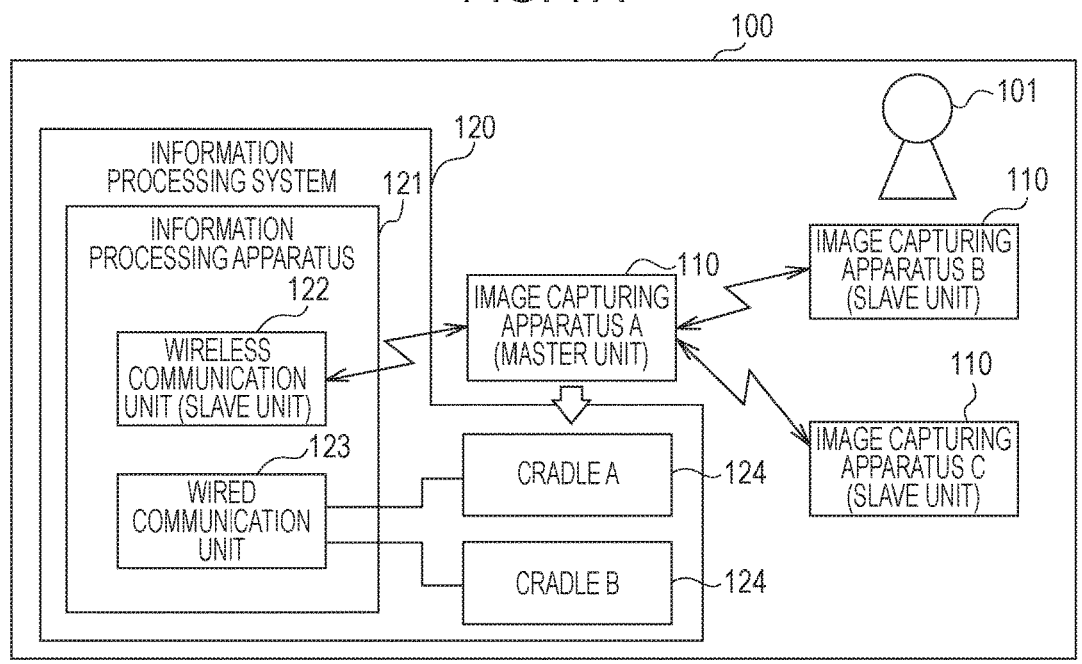
FIGS. 7A and 7B are explanatory diagrams of a communication management process.

Hereinafter, embodiments of the present invention will be described with reference to drawings. Hereinafter, radiation includes not only X-rays but also alpha rays, beta rays, gamma rays, corpuscular rays, cosmic rays, and the like.

First Embodiment

FIG. 1 is an overall configuration diagram of a radiographing system 100. The radiographing system 100 includes an X-ray generator 101, three (multiple) image capturing apparatuses 110, and an information processing system 120. The information processing system 120 includes an information processing apparatus 121 and two cradles 124. The number of cradles 124 provided in the information processing system 120 is not limited to two. Furthermore, the number of image capturing apparatuses 110 provided in the radiographing system 100 is not limited to three. Hereinafter, in the case where the three image capturing apparatuses 110 need to be distinguished from one another, they will be referred to as an image capturing apparatus A, an image capturing apparatus B, and an image capturing apparatus C in an appropriate manner. Furthermore, in the case where the two cradles 124 need to be distinguished from each other, they will be referred to as a cradle A and a cradle B.

The X-ray generator 101 performs application of X-rays. The image capturing apparatus 110 is configured such that fluorescence bodies for converting X-rays into visible light are stacked on pixels formed of photoelectric conversion elements. The image capturing apparatus 110 converts radiation into visible light by the fluorescence bodies, holds the visible light as electric charges, and forms an image from data obtained by AD-converting the read amount of electric charges. Furthermore, as another example, the image capturing apparatus 110 may not include fluorescence bodies and may convert X-rays into electric charges directly. The image capturing apparatus 110 has a wireless communication function, and transmits a captured image obtained by radiographing to the information processing apparatus 121. The image capturing apparatus 110 performs wireless communication with the other image capturing apparatuses 110 and the information processing apparatus 121 using a wireless local area network (LAN) based on, for example, IEEE 802.11 standards or the like. Each of the image capturing apparatuses 110 has both functions of an access point (master unit) for outputting radio waves and a slave unit for receiving radio waves, and performs wireless communication by selecting one of the functions. Accordingly, in the radiographing system 100 according to the first embodiment, one of the image capturing apparatuses functions as an access point (master unit), thus achieving wireless communication among the apparatuses. In the case where one of the image capturing apparatuses functions as an access point, the information processing apparatus 121 is set as a slave unit.

In the first embodiment, as illustrated in FIG. 1, explanation will be provided on the assumption that the image capturing apparatus A is set as a master unit of wireless communication and the image capturing apparatuses B and C are set to slave units. In this case, in the case where a captured image is transmitted from the image capturing apparatus B to the information processing apparatus 121, a transmission path for the captured image includes two wireless communication paths, that is, a path from the image capturing apparatus B to the image capturing apparatus A and a path from the image capturing apparatus A to the information processing apparatus 121.

The information processing apparatus 121 includes a wireless communication unit 122 which performs, as a slave unit, wireless communication with the image capturing apparatus 110, and a wired communication unit 123 which performs wired communication with the image capturing apparatus 110 connected to the cradle 124. The information processing apparatus 121 performs image processing on a captured image received via the wireless communication unit 122 or the wired communication unit 123, and displays the processed image on a display unit, which will be described later. The wired communication unit 123 may perform wired communication based on normal standards such as LAN standards or may perform customized wired communication. The information processing apparatus 121 only needs to receive captured images. Processing of the information processing apparatus 121 other than that described above is not intended to limited to an embodiment. As another example, the information processing apparatus 121 may record and manage captured images.

The cradle 124 is connected to the information processing apparatus 121 in a wired manner. When the image capturing apparatus 110 is connected to the cradle 124, wired communication between the connected image capturing apparatus 110 and the information processing apparatus 121 becomes possible. The cradle 124 also has a charging function. When the image capturing apparatus 110 is connected to the cradle 124, the cradle 124 charges a power source such as a secondary battery or a condenser which is included in the connected image capturing apparatus 110. The cradle 124 may charge a secondary battery provided inside the image capturing apparatus 110. As another example, the cradle 124 may supply power directly to the image capturing apparatus 110. The cradle 124 is an example of a wired apparatus and a power supply apparatus. In the first embodiment, the cradle 124 transmits electric power in a wired manner using a metal contact or a connector. Such electric power transmission in a wired manner achieves high speed and stability, as with wired communication, which will be described later. The cradle 124 may transmit electric power in a non-contact manner by non-contact charging or the like. With electric power transmission in a non-contact manner, charging is possible even if an electrical contact is not provided outside the image capturing apparatus 110 or the cradle 124, and excellent convenience may be achieved. Therefore, in the case where stable electric power supply is possible, electric power transmission is preferably performed in a non-contact manner. A process performed in the case where the image capturing apparatus 110 is connected to the cradle 124 will be described later with reference to FIG. 5 and the like.

FIG. 2 is a diagram illustrating a hardware configuration of the information processing apparatus 121. The information processing apparatus 121 includes a central processing unit (CPU) 201, a read only memory (ROM) 202, a random access memory (RAM) 203, a hard disk drive 204, a display unit 205, an input unit 206, and an image processing unit 207, as well as the wireless communication unit 122 and the wired communication unit 123. The CPU 201 reads a control program which is stored in the ROM 202, and performs various types of processing. The RAM 203 is used as a temporary storing region, such as a main memory and a work area of the CPU 201. The HDD 204 stores various types of information such as image data and various programs. The display unit 205 displays various types of information. The input unit 206 includes a keyboard and a mouse, and receives various operations by a user. Functions and processing of the information processing apparatus 121, which will be described later, are implemented when the CPU 201 reads a program which is stored in the ROM 202 or the HDD 204 and executes the program.

The information processing apparatus 121 manages wireless communication of each of the image capturing apparatuses 110 by using an access point (AP) table. FIG. 3 is a diagram illustrating an example of an AP table. An AP table 300 stores apparatus IDs for identifying the image capturing apparatuses 110 and setting information indicating which one of a master unit and a slave unit the apparatuses are set to, in association with each other. Specifically, in the AP table 300, setting information which indicates a master unit is associated with an apparatus ID "a" of the image capturing apparatus A. Furthermore, setting information which indicates a slave unit is associated with an apparatus ID "b" of the image capturing apparatus B and an apparatus ID "c" of the image capturing apparatus C.

FIG. 4 is a diagram illustrating a hardware configuration of the image capturing apparatus 110. The image capturing apparatus 110 includes a CPU 401, a ROM 402, a RAM 403, an HDD 404, an image capturing unit 405, a first wireless communication unit 406, a second wireless communication unit 407, and a wired communication unit 408. The CPU 401, the ROM 402, the RAM 403, and the HDD 404 are similar to the CPU 201, the ROM 202, the RAM 203, and the HDD 204, which have been described above with reference to FIG. 2. The image capturing unit 405 is configured such that fluorescence bodies for converting X-rays into visible light are stacked on pixels formed of photoelectric conversion elements, holds the visible light as electric charges, and acquires a captured image by AD-converting the read amount of electric charges, as described above. The first wireless communication unit 406 performs wireless communication as a master unit. The second wireless communication unit 407 performs wireless communication as a slave unit. The wired communication unit 408 performs wired communication with the information processing apparatus 121 via the cradle 124 when the image capturing apparatus 110 is connected to the cradle 124.

FIG. 5 is a flowchart illustrating a communication management process by the information processing apparatus 121. In S500, the CPU 201 of the information processing apparatus 121 confirms whether the image capturing apparatus 110 is connected to the cradle 124. When the image capturing apparatus 110 is connected to the cradle 124, the cradle 124 transmits to the information processing apparatus 121 connection information that indicates the image capturing apparatus 110 is connected to the cradle 124. When receiving the connection information, the CPU 201 determines that the image capturing apparatus 110 is connected. In the case where the image capturing apparatus 110 is connected (Yes in S500), the CPU 201 proceeds to S501. When the image capturing apparatus 110 is connected, the cradle 124 starts to charge the connected image capturing apparatus 110. Accordingly, an internal power source of the image capturing apparatus 110 that is set as a master unit may be prevented from being consumed and becoming unable to operate in later processing.

In S501, the CPU 201 receives from the image capturing apparatus 110 via the cradle 124 setting information indicating which one of a master unit and a slave unit the image capturing apparatus 110 that is connected to the cradle 124 is set to. Then, based on the setting information, the CPU 201 confirms which one of a master unit and a slave unit the image capturing apparatus 110 is set to. In the case where the connected image capturing apparatus 110 is set as a master unit (master unit in S501), the CPU 201 proceeds to S508. In the case where the connected image capturing apparatus 110 is set as a slave unit (slave unit in S501), the CPU 201 proceeds to S502. In S502, the CPU 201 confirms whether an image capturing apparatus 110 that is connected to a cradle 124 in a wired manner exists, except the image capturing apparatus 110 for which connection is confirmed in S500. In the case where another image capturing apparatus 110 exists (Yes in S502), the CPU 201 ends the process. In the case where another image capturing apparatus 110 does not exist (No in S502), the CPU 201 proceeds to S503.

In S503, the CPU 201 sets the image capturing apparatus 110 that is connected to the cradle 124 as a master unit of wireless communication (setting processing). That is, the CPU 201 functions as a setting unit. Specifically, the CPU 201 rewrites setting information regarding a master unit and a slave unit in the AP table 300. Furthermore, the CPU 201 performs processing for changing setting of the master unit on the wireless communication unit 122. Moreover, the CPU 201 transmits, through wired communication via the wired communication unit 123 and the cradle 124, a change instruction indicating a setting change of the master unit to the image capturing apparatus 110 that is connected to the cradle 124. When receiving the change instruction, the image capturing apparatus 110 that is connected to the cradle 124 performs a setting change for setting the image capturing apparatus 110 as the master unit, in accordance with the change instruction. Then, after completing the setting change, the image capturing apparatus 110 that is connected to the cradle 124 transmits a completion notification to the information processing apparatus 121 through wired communication.

After the processing of S503, the CPU 201 transmits, through wireless communication using the wireless communication unit 122, a change instruction to the image capturing apparatus 110 that is set as a slave unit at the time when the image capturing apparatus 110 is connected to the cradle 124 in S504. When receiving the change instruction, the image capturing apparatus 110 that is set as the slave unit performs processing for changing the setting of the master unit. Then, after completing the setting change, the image capturing apparatus 110 that is set to the slave unit transmits, through wireless communication using the second wireless communication unit 407, a completion notification to the information processing apparatus 121.

After the processing of S504, the CPU 201 waits until the wireless communication unit 122 receives a completion notification in S505. When the completion notification is received (Yes in S505), the CPU 201 proceeds to S506. In S506, the CPU 201 transmits, through wireless communication using the wireless communication unit 122, a change instruction to the image capturing apparatus 110 that is set as the master unit at the time when the image capturing apparatus 110 is connected to the cradle 124. When receiving the change instruction, the image capturing apparatus 110 that is set as the master unit performs processing for changing the setting of the image capturing apparatus 110 from the master unit to the slave unit. When completing the processing, the image capturing apparatus 110 transmits, through wireless communication, a completion notification to the information processing apparatus 121. After the processing of S506, the CPU 201 waits until a completion notification is received from the image capturing apparatus 110 for which setting is changed from the master unit to the slave unit in S507. When receiving the completion notification (Yes in S507), the CPU 201 proceeds to S508. In S508, the CPU 201 stops wireless communication using the wireless communication unit 122, and starts wired communication with the image capturing apparatus 110 that is connected to the cradle 124. The communication management process is completed, as described above.

By the process described above, the image capturing apparatus 110 that is connected to the cradle 124 is set as a master unit, and wired communication between the image capturing apparatus 110 that is connected to the cradle 124 and the information processing apparatus 121 starts. Accordingly, a transmission path for a captured image uses wireless communication between the image capturing apparatus 110 that is set as the slave unit and the image capturing apparatus 110 that is set as the master unit and wired communication between the image capturing apparatus 110 that is set as the master unit and the information processing apparatus 121. That is, only one wireless communication path is used, and there is no need to use double wireless communication bands. Therefore, the information processing system 120 is able to acquire a captured image at high speed.

Furthermore, the information processing apparatus 121 performs the processing of S503 to S507 at a timing different from a reading period during which electric charges are read from pixels. Thus, intrusion of noise components into a captured image may be suppressed. The reading period is a period during which an analog single is converted into a digital signal.

Hereinafter, specific examples of a communication management process will be described with reference to FIGS. 6A to 6C and FIGS. 7A and 7B. As illustrated in FIG. 6A, it is assumed that in the state in which the image capturing apparatus 110 is connected neither the cradle A nor the cradle B, the image capturing apparatus B that is set as a slave unit is connected to the cradle A. In this case, the connected image capturing apparatus B is set as the slave unit (slave unit in S501), and there is no image capturing apparatus 110 that is connected to the cradle 124 except the image capturing apparatus B (No in S502). Therefore, in S503, the information processing apparatus 121 sets the image capturing apparatus B as a master unit. Then, the information processing apparatus 121 first transmits a change instruction to the image capturing apparatus C (slave unit) (S504), and then transmits a change instruction to the image capturing apparatus A (master unit) (S506). By the processing described above, as illustrated in FIG. 6B, the master unit of wireless communication is changed from the image capturing apparatus A to the image capturing apparatus B, and setting information in the AP table 300 is rewritten, as illustrated in FIG. 6C.

It is assumed that the image capturing apparatus 110 has already been connected to the cradle B and the image capturing apparatus 110 that is connected to the cradle B is set as the master unit. In this case, even if the image capturing apparatus B is connected to the cradle A, due to existence of the image capturing apparatus 110 that is connected to the cradle B (Yes in S502), the information processing apparatus 121 ends the communication management process without performing processing.

Figure 7B:
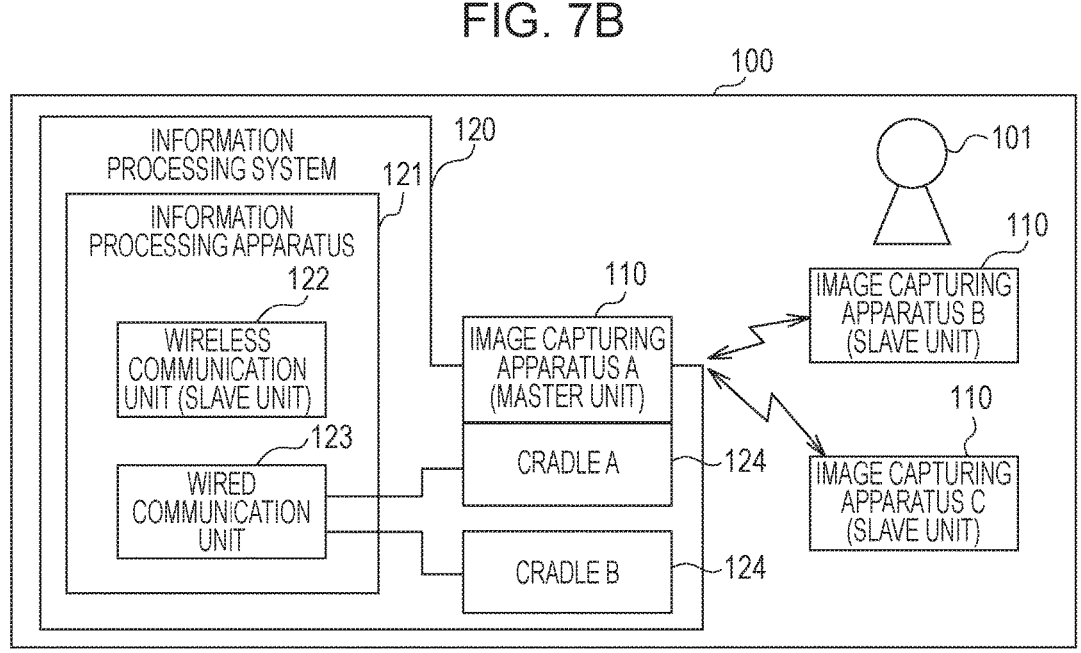

Furthermore, as illustrated in FIG. 7A, it is assumed that in the state in which the image capturing apparatus 110 is connected to neither the cradle A nor the cradle B, the image capturing apparatus A that is set as a master unit is connected to a cradle. In this case, the connected image capturing apparatus A is set as the master unit (master unit in S501). Therefore, there is no need to perform processing for setting the image capturing apparatus A to the master unit. That is, as illustrated in FIG. 7B, even after the image capturing apparatus A is connected, there is no need to change the setting of each of the image capturing apparatuses 110 to the master unit or the slave unit.

As described above, with the information processing system 120 according to the first embodiment, by setting the image capturing apparatus 110 that is connected to a cradle as a master unit, transmission of a captured image via a stable path may be achieved while preventing the communication speed from decreasing. Furthermore, when the image capturing apparatus 110 is connected to a cradle, the cradle starts to charge the image capturing apparatus 110. Therefore, a battery of the image capturing apparatus 110 that is set as the master unit does not run out.

As a first variation of the information processing system 120 according to the first embodiment, only one cradle 124 may be connected to the information processing apparatus 121. In this case, in the case where it is confirmed in S501 of the communication management process illustrated in FIG. 5 that the connected image capturing apparatus 110 serves as a slave unit, the information processing apparatus 121 may proceed to S503, without confirming whether another connected image capturing apparatus 110 exists.

As a second variation, the cradle 124 may be integrated with the information processing apparatus 121. In this case, the information processing apparatus 121 may confirm whether the image capturing apparatus 110 is connected to the information processing apparatus 121 (cradle 124), and may set the connected image capturing apparatus 110 as a master unit.

Figure 8A:
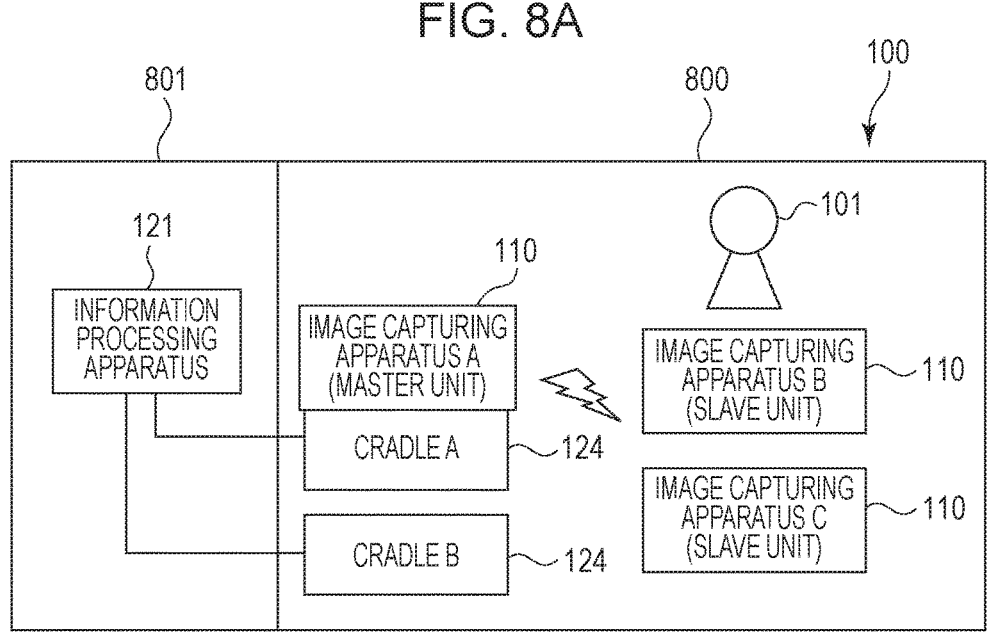
FIGS. 8A and 8B are diagrams illustrating an example of installation of the information processing apparatus.

A third variation will be described below. In the first embodiment, the case where an electromagnetic shield, such as a wall, does not exist between the information processing apparatus 121, the cradle 124, and the image capturing apparatuses 110 has been described. However, in the case where an electromagnetic shield exists between the apparatuses, the electromagnetic shield may be installed, for example, as described below. In an example of FIG. 8A, the cradle 124 is installed at an radiography room 800, and the information processing apparatus 121 is installed at an X-ray operation room 801. The radiography room 800 is a room where radiographic application to a subject for radiographic imaging and image acquisition are performed. The X-ray operation room 801 is a room where an operator performs an operation for radiography.

As described above, by installing an electromagnetic shield such as a wall such that the electromagnetic shield is not placed between the image capturing apparatus 110 that is connected to the cradle 124, that is, the image capturing apparatus 110 that is set as a master unit, and another image capturing apparatus 110, high-speed communication between apparatuses may be achieved.

Figure 8B:
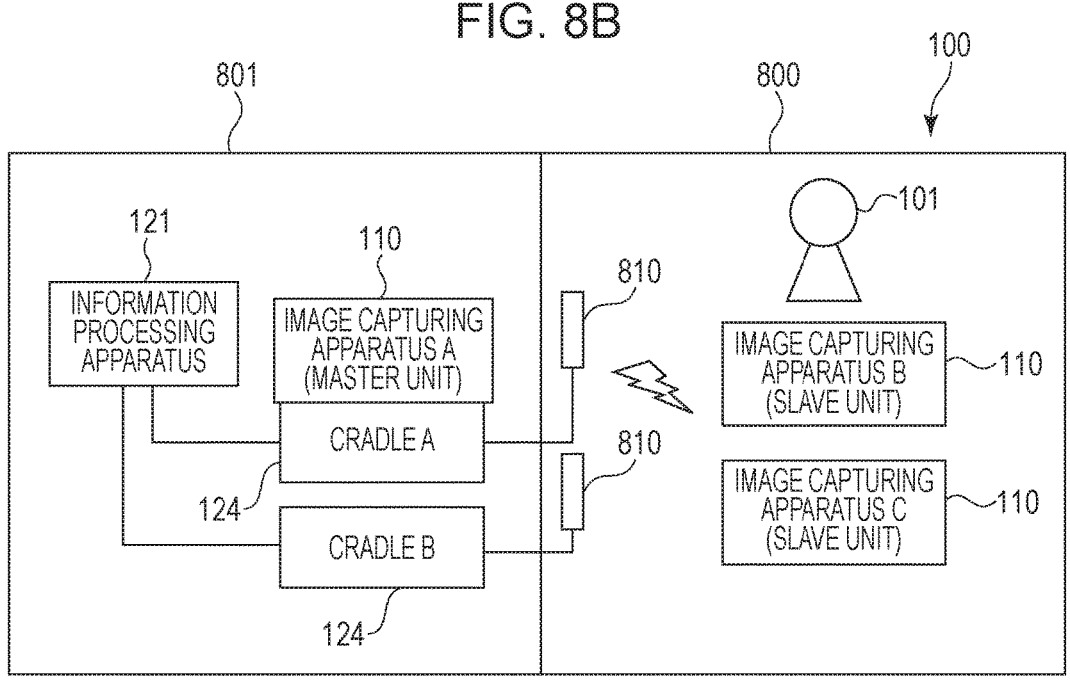

In the example of FIG. 8B, the information processing apparatus 121 and the cradles 124 are arranged in the X-ray operation room 801. In this case, an external extension antenna 810 which is connected to the cradles 124 in a wired manner is installed in the radiography room 800. Accordingly, as in the example of FIG. 8A, an electromagnetic shield is not placed between the image capturing apparatus 110 that is connected to the cradle 124 and another image capturing apparatus 110.

Figure 9A:
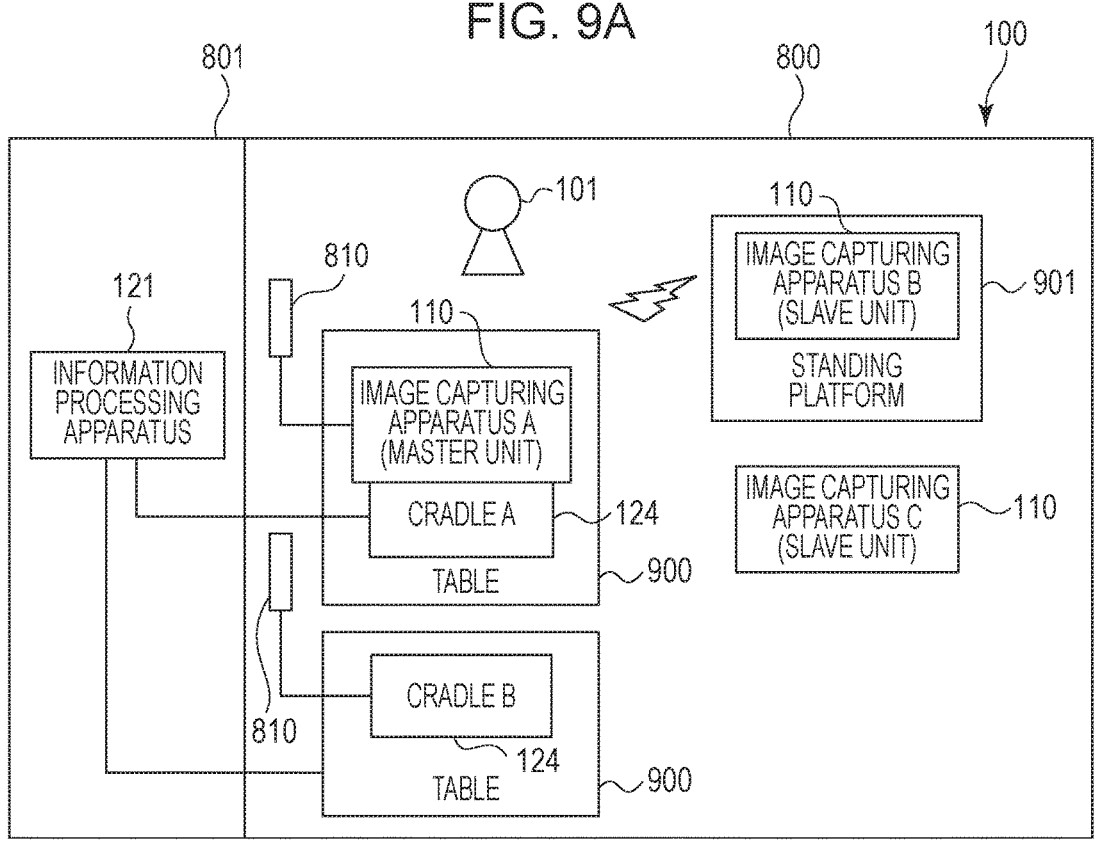
FIGS. 9A and 9B are diagrams illustrating an example of installation of the information processing apparatus.
Figure 9B:
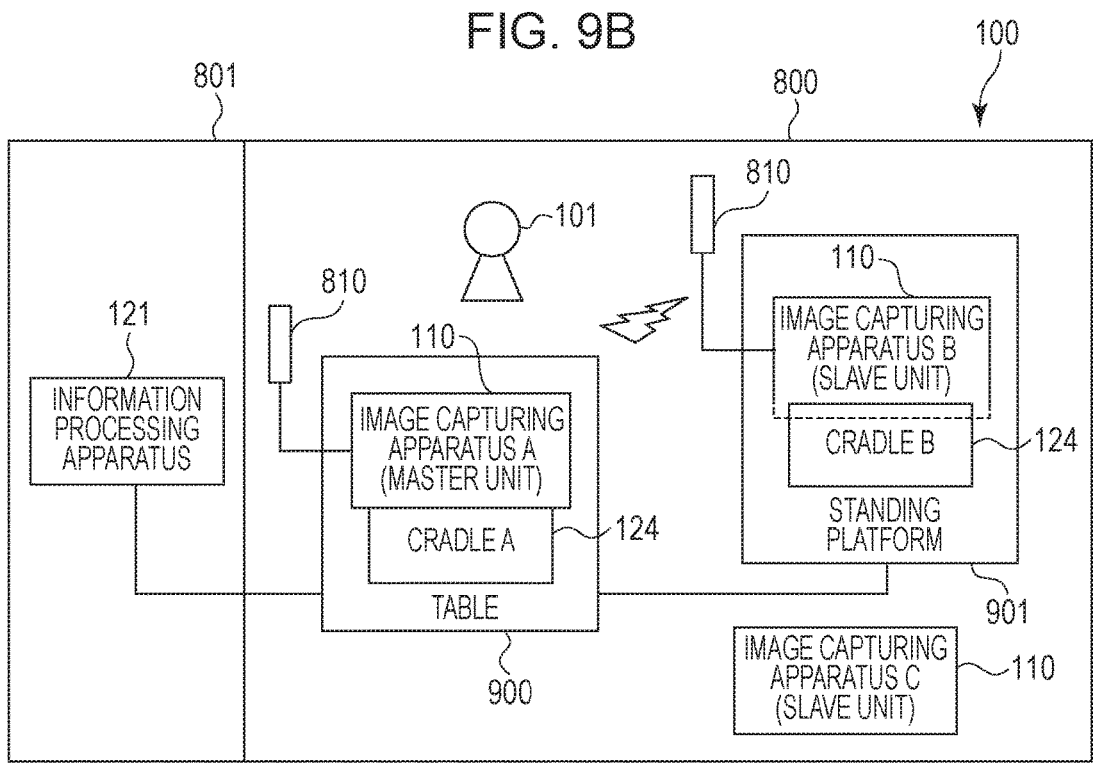

FIGS. 9A and 9B are diagrams illustrating an example in which the cradle 124 is provided within an aligning mechanism such as a table or a platform used when an image of a subject is captured. In an example of FIG. 9A, a table 900 which is installed in the radiography room 800 has a function of a cradle in a folder part of the image capturing apparatus 110. Furthermore, the external extension antenna 810 which is connected to a cradle in a wired manner is installed in the radiography room 800. Furthermore, a standing platform 901 is a cubic platform for normal radiographing. In this case, the image capturing apparatus 110 which is mounted on the standing platform 901 operates as a slave unit. In the case where the image capturing apparatus 110 is mounted on the table 900, a folder part of the mounted image capturing apparatus 110 serves as an electromagnetic shield with respect to a built-in antenna, and the electromagnetic shield may interrupt wireless communication. Therefore, a wireless communication pass is secured by the external extension antenna 810.

In an example of FIG. 9B, unlike the example of FIG. 9A, the standing platform 901 also has a function of a cradle, and the external extension antenna 810 which connected to a cradle in a wired manner is provided for the standing platform 901. Furthermore, as a wired communication path, the table 900 and the standing platform 901 are connected in a wired manner so that wireless communication is possible. Accordingly, in the case where the image capturing apparatus 110 is connected to a cradle of either the table 900 or the standing platform 901, the image capturing apparatus 110 may be set as a master unit.

In the examples illustrated in FIGS. 8A and 8B and FIGS. 9A and 9B, it is assumed that an antenna part of the wireless communication unit 122 is installed in the X-ray operation room 801 to ensure the stability of wireless communication. In the case where two or more image capturing apparatuses 110 are provided, the information processing apparatus 121 may not include the wireless communication unit 122 that is set as a slave unit.

As a fourth variation, the CPU 201 may determine whether power is supplied to an image capturing apparatus (determination processing), instead of determining whether the image capturing apparatus 110 is connected. Then, based on a determination result, the CPU 201 may set the image capturing apparatus to which power is supplied as a master unit of wireless communication (setting processing).

As a fifth variation, even after an image capturing apparatus that is connected to the cradle 124 is set as a master unit, the information processing apparatus 121 may perform wireless communication, via the wireless communication unit 122, with the image capturing apparatus that is set as the master unit. That is, the information processing apparatus 121 may receive a captured image through wireless communication.

Furthermore, as a sixth variation, the radiographing system 100 only needs to include at least one information processing apparatus 121, one cradle 124, and one image capturing apparatus 110. The number of each apparatus is not limited to an embodiment. It is assumed that a radiographing system includes one information processing apparatus 121, one cradle 124, and one image capturing apparatus 110. In this case, in the case where the image capturing apparatus is connected to the cradle or power supply to the image capturing apparatus from the cradle starts, the information processing system 120 sets the image capturing apparatus as a master unit of wireless communication. Then, the information processing apparatus receives a radiographic image captured by the image capturing apparatus that is set as a master unit.

Second Embodiment

Next, a radiographing system 100 according to a second embodiment will be described. In the radiographing system 100 according to the second embodiment, the image capturing apparatus 110 which is connected to the cradle 124 mainly performs processing regarding a setting change of a master unit of wireless communication. Hereinafter, the radiographing system 100 according to the second embodiment will be described by focusing on differences from the radiographing system 100 according to the first embodiment.

Figure 10:
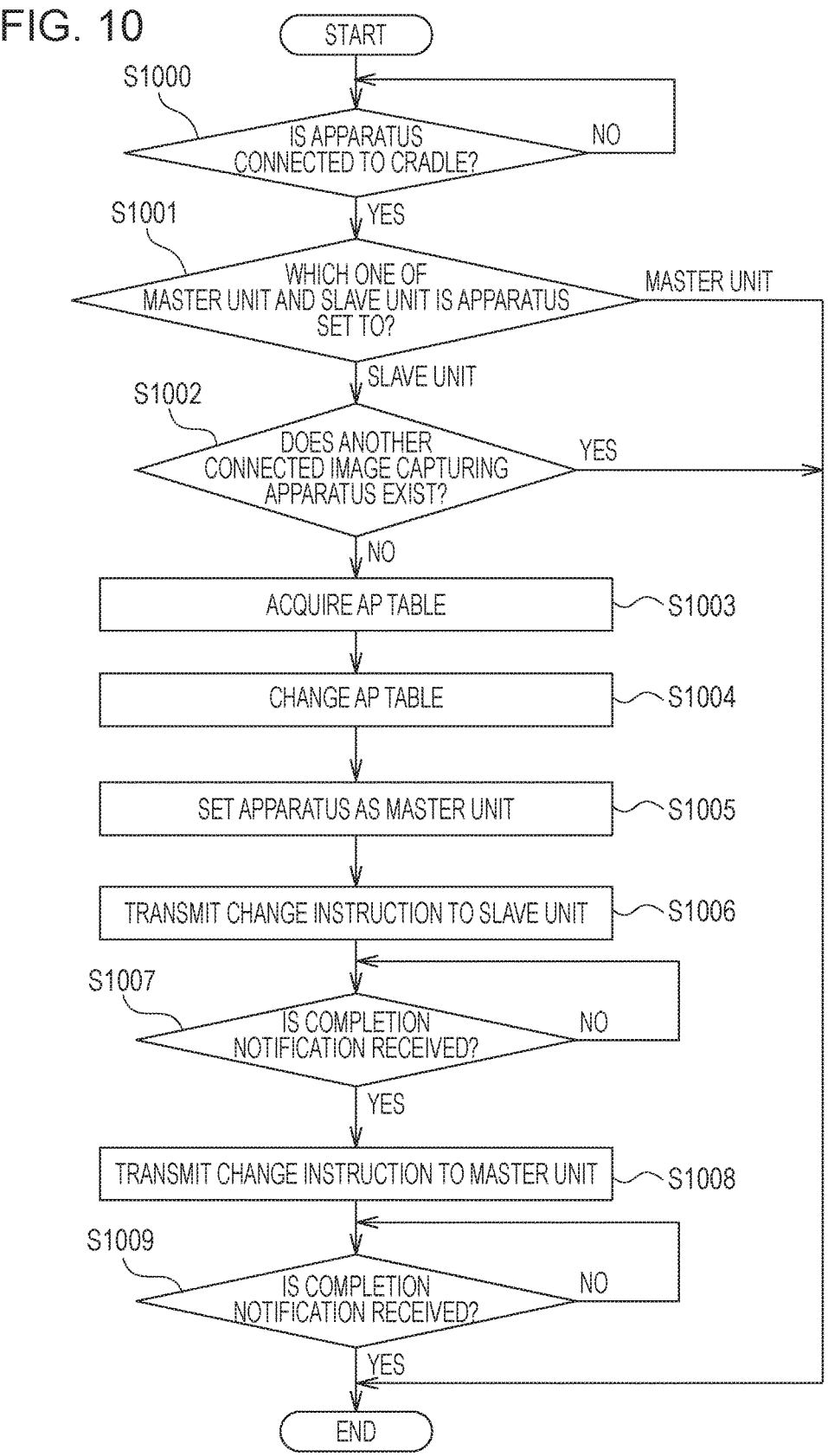
FIG. 10 is a flowchart illustrating a communication management process.

FIG. 10 is a flowchart illustrating a communication management process by the image capturing apparatus 110 according to the second embodiment. In S1000, the CPU 401 of the image capturing apparatus 110 confirms whether the image capturing apparatus 110 is connected to the cradle 124 as a wired apparatus which is connected in a wired manner to the information processing apparatus 121 to which a captured image is to be transmitted. The CPU 401 includes a connection detector (not illustrated in figures). In the case where the connection detector detects connection to the cradle 124, the CPU 401 determines that the image capturing apparatus 110 is connected to the cradle 124. When it is determined that the image capturing apparatus 110 is connected to the cradle 124 (Yes in S1000), the CPU 401 proceeds to S1001. In S1001, the CPU 401 confirms which one of a master unit and a slave unit the image capturing apparatus 110 is set to. In the case where the image capturing apparatus 110 is set as a maser unit (master unit in S1001), the CPU 401 ends the communication management process. In the case where the image capturing apparatus 110 is set as a slave unit (slave unit in S1001), the CPU 401 proceeds to S1002.

In S1002, the CPU 401 confirms whether an image capturing apparatus 110 that is connected to a cradle 124 exists except for the image capturing apparatus 110. Specifically, the CPU 401 queries the information processing system 120 through wired communication as to whether another image capturing apparatus 110 that is connected to the cradle 124 exists. The CPU 401 receives information which indicating presence or absence of another image capturing apparatus 110 from the information processing system 120, and determines, based on the received information, whether another image capturing apparatus 110 exists. In the case where another image capturing apparatus 110 exists (Yes in S1002), the CPU 401 ends the communication management process. In the case where another image capturing apparatus 110 does not exist (No in S1002), the CPU 401 proceeds to S1003.

In S1003, the CPU 401 acquires the AP table 300 from the information processing apparatus 121 through wired communication via the wired communication unit 408. In S1004, the CPU 401 rewrites setting information in the AP table 300 such that the image capturing apparatus 110 is set as a master unit, and transmits the rewritten AP table 300 to the information processing apparatus 121 through wired communication. Next, in S1005, the CPU 401 performs processing for changing the setting of the image capturing apparatus 110 to the master unit.

In S1006, the CPU 401 transmits a change instruction to the image capturing apparatus 110 that is set as a slave unit through wireless communication using the second wireless communication unit 407. When receiving the change instruction, the image capturing apparatus 110 that is set as the slave unit performs processing for changing setting of a master unit. Then, after the setting change is completed, the image capturing apparatus 110 that is set as the slave unit transmits a completion notification to the image capturing apparatus 110 that is connected to the cradle 124 through wireless communication using the second wireless communication unit 407. In S1006, the CPU 401 also transmits a change instruction to the wireless communication unit 122 of the information processing apparatus 121 that is set as a slave unit through wireless communication using the second wireless communication unit 407. Then, the wireless communication unit 122 also performs processing for changing the setting of a master unit, as with the other slave units.

After the processing of S1006, the CPU 401 waits until a completion notification is received through wireless communication via the second wireless communication unit 407 in S1007. When receiving the completion notification (Yes in S1007), the CPU 401 proceeds to S1008. In S1008, the CPU 401 transmits a change instruction to the image capturing apparatus 110 that is set as a master unit through wireless communication using the second wireless communication unit 407. When receiving the change instruction, the image capturing apparatus 110 that is set as the master unit performs processing for changing setting of the image capturing apparatus 110 from a master unit to a slave unit. When the processing is completed, the image capturing apparatus 110 transmits a completion notification to the information processing apparatus 121 through wireless communication using the second wireless communication unit 407.

After the processing of S1008, the information processing apparatus 121 waits until a completion notification is received from the image capturing apparatus 110 for which setting has been changed from a master unit to a slave unit through wireless communication via the second wireless communication unit 407 in S1009. When the information processing apparatus 121 receives a completion notification (Yes in S1009), the communication management process ends. The other features of configuration and processing of the radiographing system 100 according to the second embodiment are similar to those of the radiographing system 100 according to the first embodiment.

As described above, also in the radiographing system 100 according to the second embodiment, by setting the image capturing apparatus 110 that is connected to a cradle as a master unit, transmission of a captured image via a stable path may be achieved while preventing the communication speed from decreasing.

According to each of the foregoing embodiments, transmission of a captured image via a stable path may be achieved while preventing the communication speed from decreasing.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While aspects of the present invention have been described with reference to exemplary embodiments, it is to be understood that the aspects of the invention are not limited to the disclosed exemplary embodiments. The scope of the following claims is to be accorded the broadest interpretation so as to encompass all such modifications and equivalent structures and functions.

This application claims the benefit of Japanese Patent Application No. 2015-125895, filed Jun. 23, 2015, which is hereby incorporated by reference herein in its entirety.

What is claimed is:

1. An information processing system comprising:
an information processing apparatus configured to receive captured radiographic images captured by a plurality of image capturing apparatuses each having a wireless communication function;
a wired apparatus configured to be connected to the information processing apparatus in a wired manner;
a confirmation unit configured to confirm that, according to one of the plurality of image capturing apparatuses having been connected to the wired apparatus, the connected image capturing apparatus has been set as a slave unit;
a setting unit configured to set, according to a result of confirmation performed by the confirmation unit, the connected image capturing apparatus as a master unit of wireless communication; and
a communication unit configured to receive, via the image capturing apparatus set as the master unit by the setting unit, a captured image of a different image capturing apparatus that is received through wireless communication by the image capturing apparatus set as the master unit from the different image capturing apparatus set as a slave unit of wireless communication.

2. The information processing system according to claim 1, wherein the communication unit receives, through wired communication via the wired apparatus, the captured image from the image capturing apparatus that is set as the master unit by the setting unit.

3. The information processing system according to claim 1, further comprising a wireless communication unit configured to perform wireless communication as a slave unit, the wireless communication unit receiving, in a case where no image capturing apparatus is connected to the wired apparatus, a captured image through the wireless communication from the image capturing apparatus set as the master unit.

4. The information processing system according to claim 1, wherein after a completion notification regarding a setting change of a master unit corresponding to a change instruction is received through wireless communication from the image capturing apparatus that is set as the slave unit, the change instruction is transmitted through wireless communication to the image capturing apparatus that is set as the master unit.

5. The information processing system according to claim 1, wherein the confirmation unit further confirms that no other image capturing apparatuses are connected to the wired apparatus.

6. The information processing system according to claim 1, wherein the setting unit sets the master unit at a timing different from a period during which the image capturing apparatus reads electric charges based on radiation.

7. An information processing method performed by an information processing system including an information processing apparatus configured to receive captured radiographic images captured by a plurality of image capturing apparatuses each having a wireless communication function, and a wired apparatus configured to be connected to the information processing apparatus in a wired manner, the information processing method comprising:
a confirmation step of confirming that, according to one of the plurality of image capturing apparatuses having been connected to the wired apparatus, the connected image capturing apparatus has been set as a slave unit;
a setting step of setting, according to a result of confirmation performed in the confirmation step, the connected image capturing apparatus as a master unit of wireless communication; and a wired communication step of receiving, through wired communication via the wired apparatus from the image capturing apparatus set as the master unit, a captured image of a different image capturing apparatus that is received through wireless communication by the image capturing apparatus set as the master unit from the different image capturing apparatus set as a slave unit of wireless communication.

8. A radiographing system comprising:

a plurality of an image capturing apparatuses each configured to include a wireless communication function;

an information processing apparatus configured to receive, through wireless communication, a captured radiographic image captured by the plurality of image capturing apparatuses;

a wired apparatus configured to be connected to the information processing apparatus in a wired manner;

a confirmation unit configured to confirm that, according to one of the plurality of image capturing apparatuses having been connected to the wired apparatus, the connected image capturing apparatus has been set as a slave unit;

a setting unit configured to set, according to a result of confirmation performed by the confirmation unit, the connected image capturing apparatus as a master unit of wireless communication; and a communication unit configured to receive, via the image capturing apparatus set as the master unit by the setting unit, a captured image of a different image capturing apparatus that is received through wireless communication by the image capturing apparatus set as the master unit from the different image capturing apparatus set as a slave unit of wireless communication.

9. The radiographing system according to claim 8, wherein the image capturing apparatus includes a secondary battery, and wherein the wired apparatus charges the secondary battery as a power supply apparatus.

10. The radiographing system according to claim 9, wherein the confirmation unit further confirms that no other image capturing apparatuses are connected to the power supply apparatus.

11. An image capturing apparatus having a wireless communication function and to be used in a radiographing system including a plurality of image capturing apparatuses each having a wireless communication function, an information processing apparatus configured to receive, through wireless communication, radiographic images captured by the plurality of image capturing apparatuses, and a wired apparatus connected to the information processing apparatus in a wired manner, the image capturing apparatus comprising:

a confirmation unit configured to confirm that, according to the image capturing apparatus having been connected to the wired apparatus, the connected image capturing apparatus has been set as a slave unit;

a setting unit configured to set, according to a result of confirmation performed by the confirmation unit, the connected image capturing apparatus as a master unit of wireless communication;

a wireless communication unit configured to receive, through wireless communication, a captured image captured by another image capturing apparatus set as a slave unit of the wireless communication from the another image capturing apparatus; and a wired communication unit configured to transmit, via the wired apparatus in a wired manner, the captured image captured by the another image capturing apparatus received by the wireless communication unit.

12. The image capturing apparatus according to claim 11, wherein the setting unit is configured to rewrite setting information about a master unit and a slave unit obtained by the wired communication unit via the wired apparatus from the information processing apparatus, and wherein the wired communication unit is configured to transmit the rewritten setting information about the master unit and the slave unit to the information processing apparatus via the wired apparatus.

13. The image capturing apparatus according to claim 11, further comprising:

a secondary battery, wherein the secondary battery is charged by the wired apparatus.

14. The image capturing apparatus according to claim 11, wherein the confirmation unit is further configured to confirm that no other image capturing apparatuses are connected to the wired apparatus.

* * * * *